US005696158A

United States Patent [19]
Oliver

[11] Patent Number: 5,696,158
[45] Date of Patent: *Dec. 9, 1997

[54] LOUSE REPELLENT

[75] Inventor: William John Oliver, Darby Green, United Kingdom

[73] Assignee: Unicliffe Limited, Kent, England

[*] Notice: The term of this patent shall not extend beyond the expiration date of Pat. No. 5,496,852.

[21] Appl. No.: 470,128

[22] Filed: Jun. 6, 1995

Related U.S. Application Data

[63] Continuation of Ser. No. 255,822, Jun. 8, 1994, Pat. No. 5,496,852, which is a continuation of Ser. No. 761,360, Aug. 28, 1991, abandoned.

[30] Foreign Application Priority Data

Feb. 28, 1989 [GB] United Kingdom ............ 89 04 541.3

[51] Int. Cl.$^6$ ...................... A01N 43/26; A01N 35/00; A01N 31/08
[52] U.S. Cl. ...................... 514/463; 514/693; 514/734; 514/918; 514/919; 424/DIG. 10
[58] Field of Search ...................... 514/463, 693, 514/734, 918, 919; 424/DIG. 10

[56] References Cited

U.S. PATENT DOCUMENTS

| | | | |
|---|---|---|---|
| 3,948,952 | 4/1976 | Gates et al. | 260/340.5 |
| 4,762,718 | 8/1988 | Marks, Sr. | 424/409 |
| 4,933,371 | 6/1990 | Hink et al. | 514/739 |
| 5,496,852 | 3/1996 | Oliver | 514/463 |

FOREIGN PATENT DOCUMENTS

| | | |
|---|---|---|
| A 0143297 | 6/1985 | European Pat. Off. . |
| 2 222 949 | 3/1990 | United Kingdom . |

OTHER PUBLICATIONS

Chemical Patents Index, Basic Abstracts Journal, Section C, Week B26, 22 Aug. 1979, Derwent Publications Ltd. (London, GB) p. 53, Abstract 48041 & JP, A, 54062316.
G.W. Eddy et al., Chem. Abs., vol. 49, 1267 h (1954).
G.W. Eddy, Chem. Abs., vol. 41, 1947, col. 4885 b–d.
The Merck Index, Tenth Edition, 1983, Merck & Co., Inc., (Rahway, N.J., US), p. 1078, compound No. 7350.
R.H. Wright, "Why Mosquito Repellents Repel," *Scientific American*, vol. 233, pp. 104–111, 1975.
Windholz et al., *The Merck Index*, p. 1078; Abs. No. 7350 (1983).

*Primary Examiner*—Kevin E. Weddington
*Attorney, Agent, or Firm*—Woodcock Washburn Kurtz Mackiewicz & Norris, LLP

[57] ABSTRACT

A pediculicidal composition is provided which is effective against both adult lice and lice eggs and additionally exhibits a strong repellent effect on adult lice. The active ingredient is piperonal which is generally used in solution at a concentration of at least 3%. An additional component of the composition is a film-forming material which is capable of holding the piperonal in contact with the host for at least two hours.

15 Claims, No Drawings

LOUSE REPELLENT

This is a continuation of application Ser. No. 08/255,822, filed Jun. 8, 1994, now U.S. Pat. No. 5,496,852, issued Mar. 5, 1996, which is a continuation of application Ser. No. 07/761,360, filed Aug. 28, 1991 now abandoned.

The present invention relates to pediculicidal compositions and includes a method of controlling louse infestations.

Head lice are a common health problem and spread rapidly in institutions such as the Armed Services and in schools. One of the difficulties in controlling head lice is that the eggs attach themselves very firmly to the base of hairs by adhesive secretions which makes them difficult to remove. Second, the eggs are protected by a waxy cuticle which is not penetrated by currently available anti-louse preparations. Conventional methods of controlling head lice therefore depend on the use of a medicated shampoo or lotion which loosens the natural adhesive or gum which binds the eggs to the hair of the scalp and at the same time is toxic to the hatched and active lice.

Although many of these conventional preparations are satisfactory in some cases if used conscientiously, their success does depend on very thorough repetitive treatments over a long period. They also have the disadvantage that many of the louse repellants which are used have unpleasant smells and this discourages their proper and continuous use over the required period of treatment.

We have now discovered that a compound which is related to benzaldehyde is very effective as a louse repellant.

In its broadest aspect the invention provides a pediculicidal and lice repellent composition which is effective against adult lice and lice eggs which comprises a solution of piperonal, said solution containing a component which maintains the piperonal in solution in contact with the host for at least 2 hours.

Piperonal is an aromatic aldehyde, and has the formula:

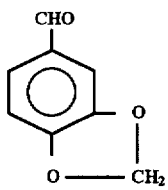

and its preparation is given in U.S. Pat. No. 2,916,499 and J Org. Chem. 26, 4814 (1961).

In the past, piperonal has been used quite widely as a constituent of perfumes and flavours, at relatively low concentrations, e.g. 50 ppm, giving a sweet floral tone to fragrances.

Piperonal is soluble in alcohols, glycols end some oils.

In the practice of the present invention, it is fairly important that the piperonal is maintained in solution since it is not as effective in its solid state. Although piperonal is soluble in lower alcohols, e.g. ethanol or isopropanol, the alcohol tends to separate leaving crystalline piperonal deposited on the body or hairs of the host. It has been found that a long-lasting repellent action is achieved by incorporating a hydrophilic film-forming component with the composition. Although not fully established, it is believed that the hydrophilic film-forming component reduces the rate of evaporation of the solvent, thus preventing crystallisation. Whatever the precise mechanism of this advantageous effect, formulations which contain the film-forming component have been shown to exhibit a strong repellent effect towards lice which lasts for up to 6 to 8 hours after the application to the hair.

Solutions of piperonal containing about 1% of the active ingredient ere generally not very active. A concentration of at least about 3% by weight is generally desirable and we prefer compositions containing at least 4% by weight of piperonal. There is no critical upper limit but there is usually no advantage in using more than 10% by weight.

According to the preferred form of the invention there is provided a pediculicidal and lice repellent composition for controlling head lice which comprises a solution of 4 to 10% by weight of piperonal and a film-forming component which is substantive to the hair of the host and is capable of maintaining the piperonal in solution in contact with the hair of a host for at least 2 hours.

Preferably, the film-forming component is a hydrophilic polymer and is preferably present in an amount of from 0.3 to 3% by weight. Examples of preferred film-forming components are a vinyl pyrrolidone polymer, a vinyl acetate polymer, a quarternized collagen, a quarternized cellulose derivative or a polymer containing hydroxy and amino groups.

As indicated above, piperonal is soluble in alcohols, glycols and some oils, particularly terpene oils. Ethanol or propanol is conveniently used as the main solvent. However, in order to reduce its rate of evaporation, higher alcohols, glycols, compatible oils and/or water may be included in the formulation. For example, the solvent may comprise 50 to 70%. ethanol or propanol. Terpenes are a preferred optional ingredient, particularly if maximum ovicidal properties are desired. It is a property of terpenes that they enhance the penetration by the piperonal of the waxy cuticle of the lice eggs. Another desirable optional component is an aliphatic long chain hydrocarbon, which appears to enhance the wetting of the skin of the lice with the pediculicidal compositions.

The following Examples in which all percentages are by weight give illustrative louse repellent compositions in accordance with the invention.

The ingredients specified in the following Examples were mixed in the amounts stated to give the corresponding formulations.

EXAMPLE 1

Piperonal Lotion with terpenes and long chain alkanes
Piperonal 5.0% w/w
Long chain alkane mixture (Shellsol T) 5.0% w/w
Terpineol 8.2% w/w
d-Limonene 5.3% w/w
iso Propyl Alcohol 76.5% w/w
Shellsol T is a complex mixture of long chain alkanes.
Terpineol and d-Limonene are naturally occurring terpenes with fairly high boiling points.

EXAMPLE 2

Piperonal Lotion with Essential Oil and Copolymeric Resin
Piperonal 5.0% w/w
Thyme Oil 0.5% w/w
Isopropyl myristate 2.0% w/w
Propylene Glycol 10.0% w/w
Adipic acid copolymer resin (Cartaretin F) 1.0% w/w
iso Propyl Alcohol 50.0% w/w
Water 31.5% w/w
Thyme oil is a volatile oil distilled from THYMUS VULGARIS comprises mainly of Thymols and carvacrol. It is a counter-irritant.

Cartaretin F is an Adipic acid/Dimethylamino hydroxy propyl diethylene triamine copolymer. It is a hair fixative.

EXAMPLE 3

Piperonal Lotion with Soluble Lanolin
Piperonal 5.0% w/w
Soluble Lanolin (Lanexol AWS) 2.0% w/w
Ethanol 60.0% w/w
Water 33.0% w/w Soluble lanolin is a modified lanolin. Lanolin is a complex natural wax comprising of esters and polyesters of long chain fatty acids and fatty alcohols.

EXAMPLE 4

Piperonal Lotion with PVP/VA Copolymer Resin
Piperonal 5.0% w/w
PVP/VA resin (Kollidon VA 64) 1.0% w/w
Ethanol 60.0% w/w
Water 34.0% w/w PVP/VA is a polyvinyl pyrrolidone/vinyl acetate copolymer resin. It is a water soluble film former.

EXAMPLE 5

Piperonal Lotion with Polymer Resin
Piperonal 5.0% w/w
PVP (Kollidon 90) 1.0% w/w
Ethanol 60.0% w/w PVP is a polyvinyl pyrrolidone polymeric resin. It is a water soluble film former.

EXAMPLE 6

Piperonal Lotion with Quarternized Collagen Protein
Piperonal 5.0% w/w
Quarternized Collagen Protein (Crotein Q) 0.5% w/w
Ethanol 60.0% w/w
Water 34.5% w/w Quarternized Collagen protein is a quarternary ammonium derivative of hydrolysed collagen protein. It is a water soluble, highly substantive conditioner.

EXAMPLE 7

Piperonal Lotion with Modified Silicone Fluid
Piperonal 5.0% w/w
Modified Silicone Fluid (Dow Corning 190) 1.0% w/w
Ethanol 60.0% w/w
Water 34.0% w/w Modified silicone fluid (Dow Corning 190) is a Silicone glycol copolymer. It is a wetting and spreading agent.

EXAMPLE 8

Piperonal Lotion with Quarternized Cellulose
Piperonal 5.0% w/w
Quarternized cellulose (CrodaCel QL) 1.0% w/w
Ethanol 60.0% w/w
Water 34.0% w/w Quarternized cellulose derivatives are produced by quarternization of hydroalkyl celluloses with a range of alkyl groups. They are conditioning aids.

Other compounds may be included in the compositions of this invention, which are pediculicidal e.g. malathion or carbaryl sevin, although this is not essential.

In the treatment of head lice the piperonal containing formulation is applied to the hair and left in contact for periods between two to twelve hours. Other additives may be included in the preparation, e.g. surfactants to increase the wetting of the hair and ingredients to depress the rate of evaporation of the solution.

The compositions of the present invention have several advantages over conventional anti-louse compositions. In particular they exhibit superior repellent activity against adult lice. Moreover, because piperonal has a pleasant smell and is approved by government licensing authorities as a food additive, there is no danger of any health risk in using the compositions nor any antipathy among infected persons against acceptance of treatment.

While the invention has been described with particular reference to combating head lice infestations, the compositions of the invention are also effective in the same way against other lice, e.g. crab lice, clothing lice and body lice.

I claim:

1. A composition for repelling lice comprising, a solution of about 1 to 10% by weight of piperonal, water, ethanol, propanol, up to 10% by weight of at least one additional alcohol which assists in maintaining the piperonal in solution in contact with the hair of the host, by reducing the rate of evaporation and suppressing crystallization of piperonal for at least 2 hours, and further comprising at least one oil, excluding terpene oils.

2. The composition of claim 1 which comprises from about 1 to 3% by weight piperonal.

3. The composition of claim 1 which further comprises a hydrophilic film-forming component selected from a vinyl pyrrolidone polymer, a vinyl acetate polymer, a quarternized collagen, a quarternized cellulose derivative, or a polymer containing hydroxy and amino groups.

4. A composition according to claim 3 in which the film-former is present in an amount of from about 0.3 to 3% by weight.

5. A composition for repelling head and body lice when maintained in solution in contact with the hair of a potential host, said composition comprising a solution of about 1 to 10% by weight of piperonal, water and at least one alcohol which is capable of maintaining the piperonal in solution in contact with the hair of the host by reducing the rate of evaporation .and suppressing crystallization of piperonal for at least 2 hours.

6. A composition for repelling head and body lice when maintained in solution in contact with the hair of a potential host, said composition comprising a solution of about 1 to 10% by weight of piperonal in an aqueous alcohol selected from ethanol and propanol, and at least one additional alcohol which assists in maintaining the piperonal in solution in contact with the hair of said host, by reducing the rate of evaporation and suppressing crystallization of piperonal for at least 2 hours.

7. The composition of claim 1 which comprises from about 1 to 3% by weight piperonal.

8. The composition of claim 6 further comprising at least one oil, excluding terpene oils.

9. A lice repellent composition which is effective against adult lice, said composition comprising, a solution of piperonal, said solution containing a hydrophilic film-forming component, ethanol or propanol, and an aliphatic long chain hydrocarbon to enhance the wetting of the skin of the lice with the lice repellent.

10. The repellent composition of claim 9, wherein said long chain hydrocarbon is a mixture of alkanes.

11. A composition for repelling head and body lice when maintained in solution and in contact with the hair of a potential host, said composition comprising a solution of about 1 to 3% by weight of piperonal in an aqueous alcohol selected from ethanol and propanol, and at least one additional alcohol which assists in maintaining the piperonal in solution when in contact with said hair of said host, by reducing the rate of evaporation and suppressing crystallization of piperonal for about 2 to 12 hours.

12. A composition of claim 11 further comprising a higher alcohol.

13. The composition of claim 11 further comprising a hydrophilic film forming agent.

14. The composition of claim 11 wherein said solution comprises about 50 to 70% by weight of ethanol or propanol.

15. A composition for repelling head and body lice when maintained in solution and in contact with the hair of a potential host, said composition comprising a solution of about 1 to 3% by weight of piperonal in an aqueous alcohol selected from ethanol and propanol, and at least one additional alcohol which assists in maintaining the piperonal in solution when in contact with said hair of said host, by reducing the rate of evaporation and suppressing crystallization of piperonal for from about 2 to 12 hours, said composition further comprising at least one oil, excluding terpene oils, whereby said lice are substantially repelled from said hair such that the potential host is protected from infestation.

* * * * *